(12) United States Patent
Kesler et al.

(10) Patent No.: US 7,334,678 B2
(45) Date of Patent: Feb. 26, 2008

(54) GUIDEWIRE HOOPS AND METHODS PERTAINING THERETO

(75) Inventors: Boris Kesler, Pembroke Pines, FL (US); Yudit Candocia, Bradenton, FL (US); Otto E. Anderhub, Miami, FL (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 450 days.

(21) Appl. No.: 10/778,745

(22) Filed: Feb. 13, 2004

(65) Prior Publication Data

US 2005/0178684 A1    Aug. 18, 2005

(51) Int. Cl.
*B65D 83/10*    (2006.01)

(52) U.S. Cl. .................. 206/364; 206/303; 206/438

(58) Field of Classification Search ................ 206/225, 206/227, 63.3, 303, 364, 388, 438, 363; 606/192; 600/439, 585
See application file for complete search history.

(56) References Cited

U.S. PATENT DOCUMENTS

| | | | |
|---|---|---|---|
| 2,920,394 A | 1/1960 | Soderbergh | |
| 3,902,679 A | 9/1975 | Bost | |
| 4,607,746 A * | 8/1986 | Stinnette | 206/53 |
| 4,903,826 A * | 2/1990 | Pearce | 206/63.3 |
| 5,125,416 A | 6/1992 | Phillips et al. | |
| 5,344,011 A | 9/1994 | DiBernardo et al. | |
| 5,507,300 A | 4/1996 | Mukai et al. | |
| 5,575,382 A | 11/1996 | Sobel et al. | |
| 6,053,313 A | 4/2000 | Farrell et al. | |
| 6,139,540 A | 10/2000 | Rost et al. | |
| 6,375,006 B1 | 4/2002 | Samuels | |
| 6,511,573 B1 | 1/2003 | Globensky et al. | |

\* cited by examiner

*Primary Examiner*—David T. Fidei
(74) *Attorney, Agent, or Firm*—Crompton, Seager & Tufte LLC

(57) ABSTRACT

A device comprising an elongated tubular member having a first open end, a second open end and a lumen therebetween, the first end and the second end facing in the same direction and positioned so that a first end of a guidewire can extend beyond the device out of the first open end and a second end of the guidewire can extend beyond the device out of the second open end and parallel to the first end of the guidewire and a method of manufacturing and packaging a guidewire comprising the steps of providing a dual distal tip guidewire having a first tip and a second tip, providing a coiled elongated tubular device having a first open end positioned proximate and facing in the same direction as a second open end, and positioning the guidewire in the tubular device.

4 Claims, 3 Drawing Sheets

GUIDEWIRE HOOPS AND METHODS PERTAINING THERETO

FIELD

The present invention pertains to devices for retaining a guidewire for processing and packaging and methods of processing and packaging a guidewire.

BACKGROUND

There are guidewires having two functional distal tips, each of which is configured to be inserted endovascularly into a patient. A treating physician may therefore select a more appropriate tip for a particular operation. During the manufacture of these guidewires, the same processing operations often need to be performed on both tips. It would be convenient to perform both of these operations simultaneously. Once the guidewire is manufactured, it needs to be packaged for storage and shipment. Packaging the guidewire after the processing operations on the tip are finished increases the risk of damage to the guidewire and the tips.

SUMMARY

One embodiment pertains to a guidewire containing device which is both a manufacturing tool and a packaging tool. The guidewire containing device comprises a coiled tubular member. The coiled tubular member has a first open end positioned proximate and facing in substantially the same direction as a second open end. This may be done by coiled a portion of the tubular member and having an s-shaped portion of the tubular member. The s-shaped portion may be a central portion or an end portion of the tubular member. The coiled tubular member may be retained in place through the use of clips, or other suitable method. A dual distal tip guidewire may therefore be placed within the coiled tubular member with the tips of the guidewire extending from the open ends of the tubular member and exiting on the same side.

Another embodiment pertains to a guidewire containing device comprising a plurality of tubular members. The lumens of the tubular members may be configured to provide a path for a guidewire similar to that of the above embodiment. There may also be a gap between the plurality of tubular members such that when a guidewire is contained in the containing device a central portion of the guidewire is exposed.

Another embodiment pertains to a method of manufacture and packaging. A guidewire may be inserted into a coiled guidewire containing device such as, for example, one of the embodiments described above so that the two ends of the guidewire extend out from the containing device proximate to each other and in the same direction. Certain manufacturing operations such as dipping, coating, curing, cleaning, or inspecting, for example, may then be performed on the guidewire ends simultaneously. Guidewire tip protectors may then be installed on the ends of the guidewire.

The above summary of some example embodiments is not intended to describe each disclosed embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings in which.

DETAILED DESCRIPTION OF SELECTED EMBODIMENT

The following detailed description should be read with reference to the drawings in which similar elements in different drawings are numbered the same. The drawings, which are not necessarily to scale, depict illustrative embodiments and are not intended to limit the scope of the invention.

Figure 1:
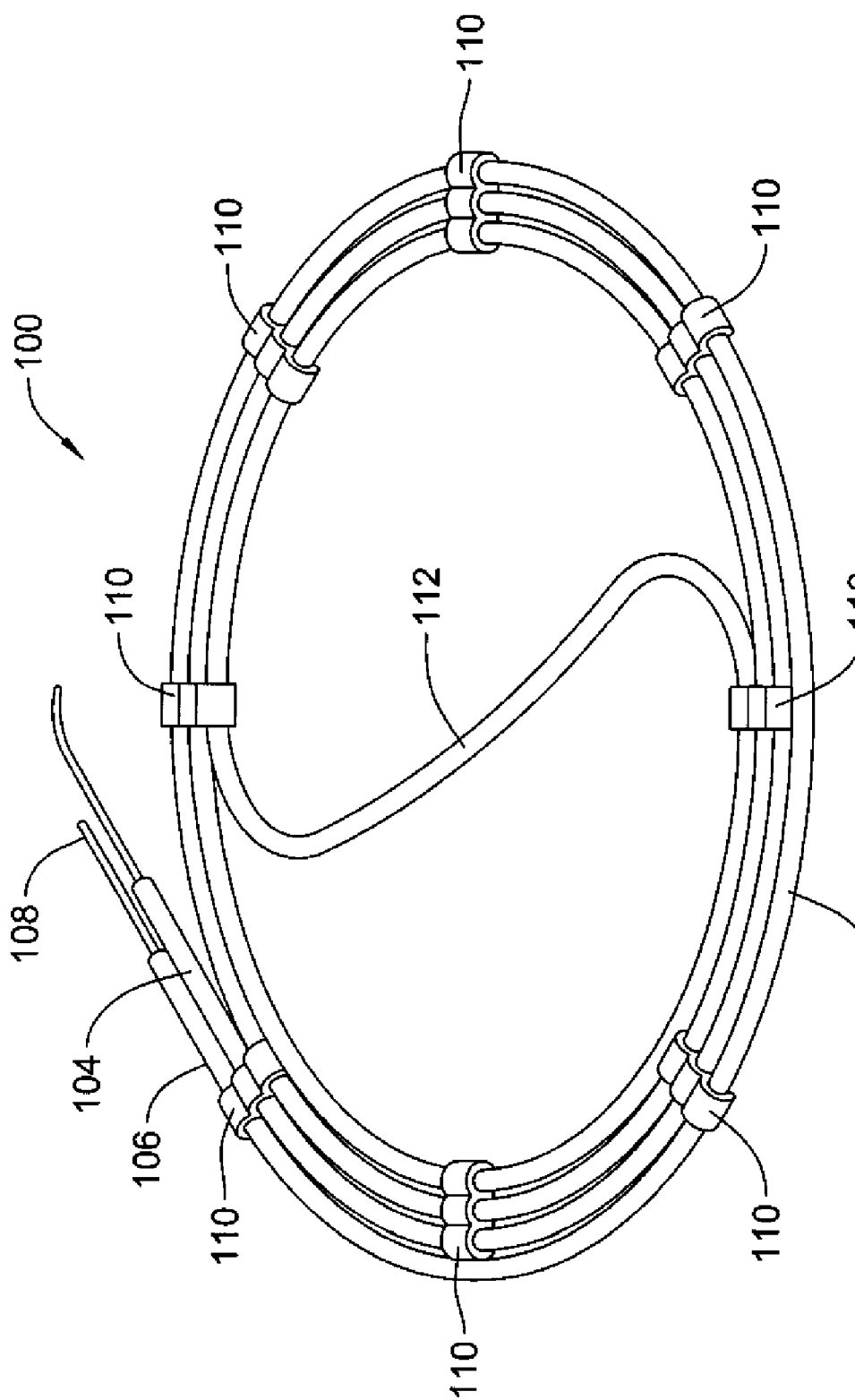
FIG. 1 is a perspective view of an example guidewire container device 100 in use.

FIG. 1 is a perspective view of an example guidewire containment device 100 which comprises an elongated tubular member 102 having a first open end 104 and a second open end 106 and a lumen therebetween. Disposed within device 100 may be a dual distal tip guidewire 108. Tubular member 102 is arranged so that ends 104 and 106 are preferably near each other and facing in the same general direction. Ends 104 and 106 are shown in FIG. 1 with no coils disposed between them. Other configurations where the ends are further apart yet still able to direct the guidewire tips in the same general direction are contemplated. The tubular member 102 may be retained in position with one or more clips 110. Clips 110 may be able to retain two, three, four, or more coil segments with respect to each other. The number and configuration of the coil segments is determined by the length of the pertinent guidewire. The coil arrangement may permit the tips of the guidewire to extend from both ends 104 and 106 of tubular member 102. The coils should preferably be arranged to permit a guidewire to be smoothly disposed therein and no coil segment should be so tight as to cause the guidewire to kink. Therefore, there may be an s-shaped segment 112 of the tubular member or other suitable configuration.

The tubular member may be made from a flexible polymer such as high-density polyethylene or polypropylene, or other suitable material such as a woven tube. The tubular member may be transparent or translucent to permit visualization of the guidewire. It may be advantageous to select a material which has a relatively lubricious inner surface. The clips may be made from plastic, resin, metal or other suitable material.

Figure 2:
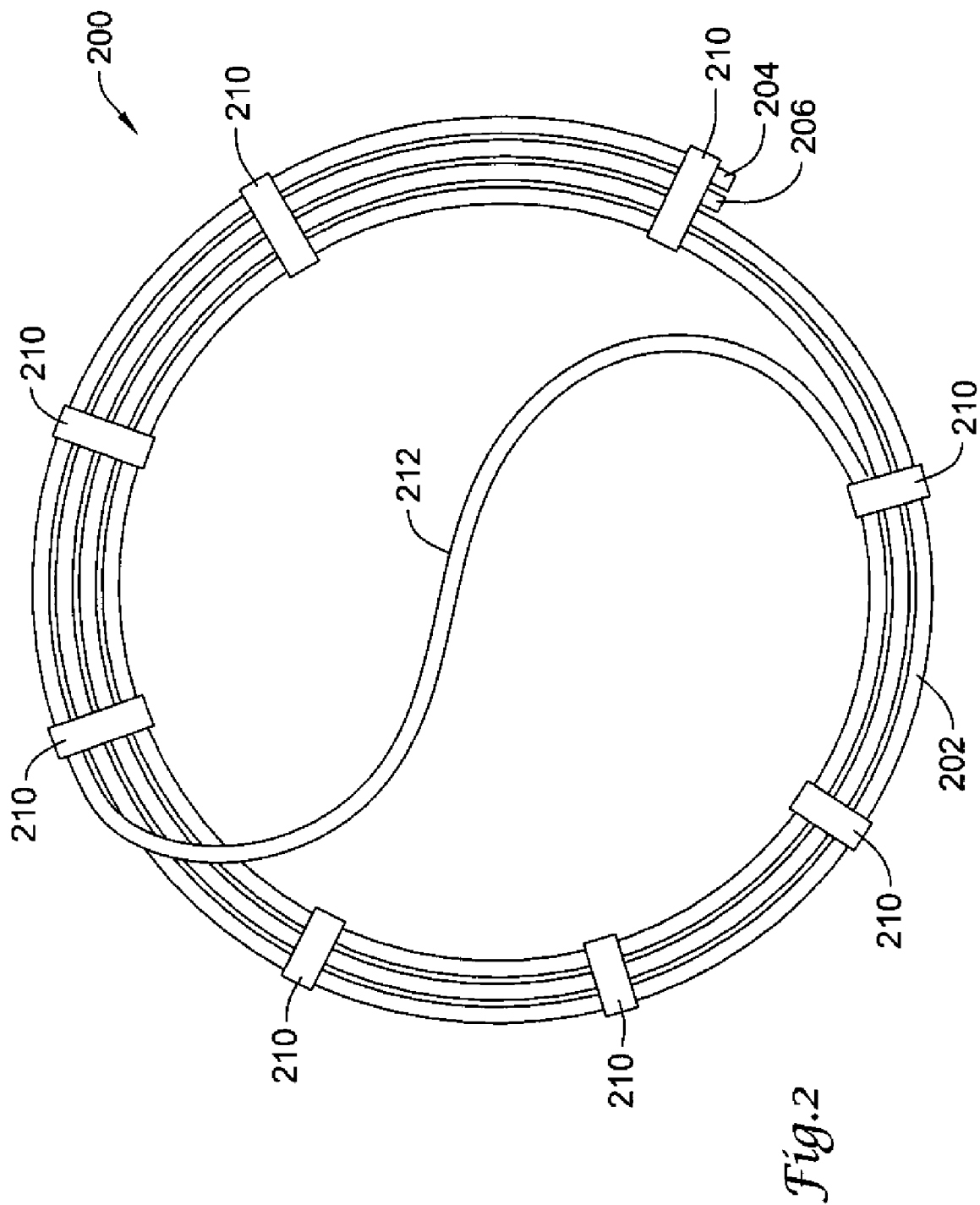
FIG. 2 is a top view of another example guidewire container device 200 in use.

FIG. 2 is a top view of an example guidewire containment device 200. Device 200 comprises an elongated tubular member 202 which has a first end 204 proximate a second end 206. Clips 210 retain tubular member 202 in the desired configuration. Guidewire tip protectors (not shown) may be slipped over the tips of the guidewires, if desired. Some clips 210 may have one or more receiving slots for receiving and retaining guidewire tip protectors. S-shaped segment 212 is positioned over other coil segments. This may increase the size of the curves in the s-shaped segment and permit the easier insertion and removal of a guidewire. In another contemplated embodiment, the innermost coil segment crosses over other coil segments to be an outer coil segment before becoming s-shaped. This may further increase the size of the smallest curves in the device, which may be desirable.

Figure 3:
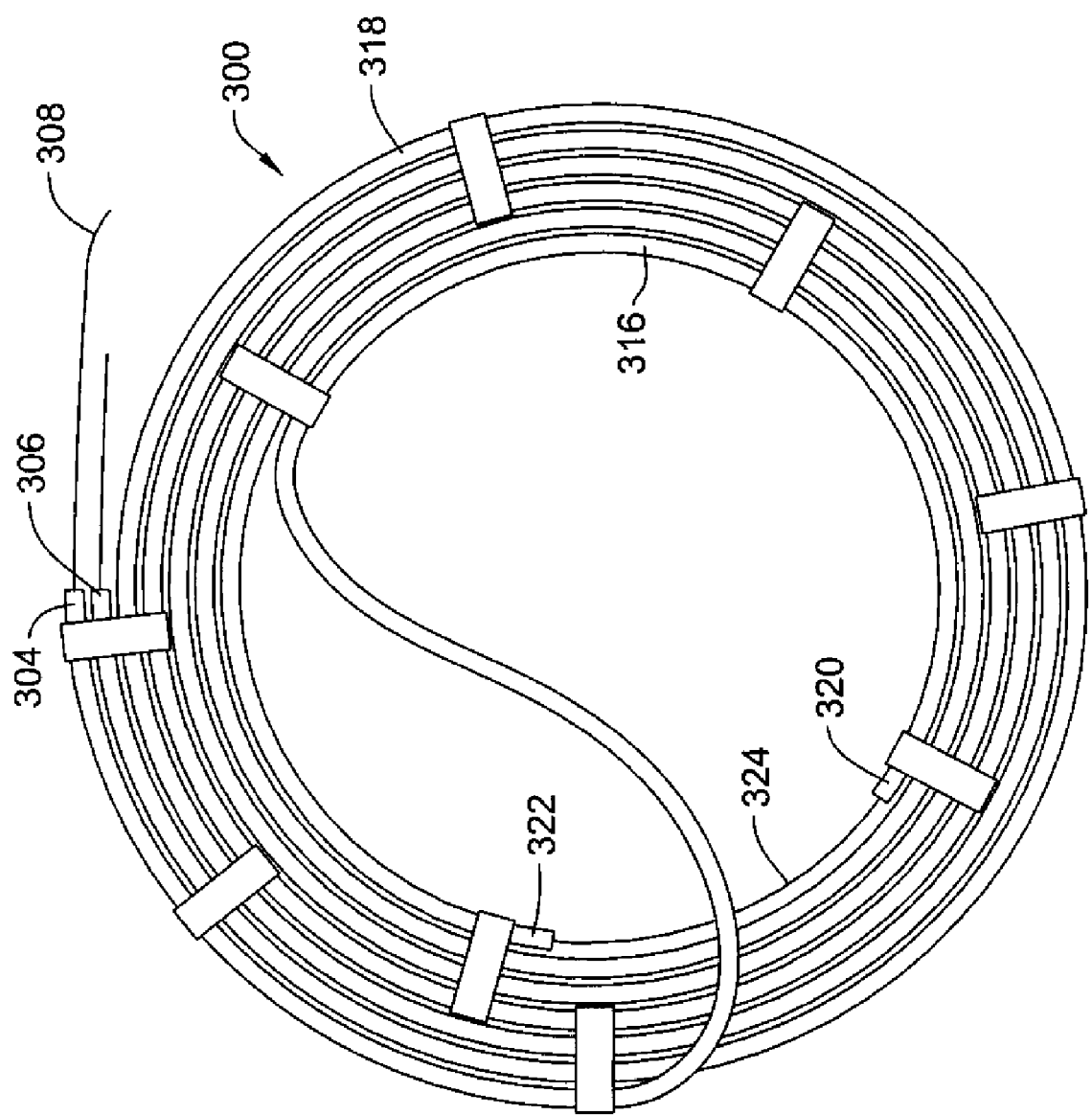
FIG. 3 is a top view of another example guidewire container device 300 in use; and While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

FIG. 3 is a top view of an example guidewire containment device 300. Device 300 comprises a first elongated tubular member 316 and a second elongated tubular member 318. Tubular member 316 has a first end 304 which is proximate and facing in the same direction as a first end 306 of tubular member 318. Tubular member 316 has a second end 320 which generally faces along a curve a second end 322 of tubular member 318. There is generally a gap between ends 320 and 322 and these ends and the gap may be conveniently located on the innermost loop of the device, as shown. When a guidewire 308 is inserted into the device, this configuration leaves an exposed intermediate segment 324 of the guidewire. This configuration may therefore aid in the loading of the guidewire into the device.

Of course, other embodiments are contemplated. For example, the guidewire containment device may be made from rigid molded or milled plastic without the use of clips. As an alternative to clips, a tubular member may be fused or glued in position, perhaps on a separate support structure.

In use, a dual distal tip guidewire may be loaded into a guidewire containment device so that the distal tips of the guidewire extend from the device in generally the same direction. While in the containment device, the guidewire tips may be processed. For example, both tips may be readily ultrasonically cleaned simultaneously in the same ultrasonic cleaning machine. This may be done, of course, because the containment device positions the tips near each other and facing in the same general direction. Other example processes which may be performed on the tips simultaneously include coating, dipping, and curing. Once the desired processes are performed, the containment device is left on the guidewire for packaging and protection purposes. Not needed to move the guidewire from a manufacturing tool to a packaging device lessens the chances of damaging the guidewire and the tips. Guidewire tip protectors may then be installed and the assembly may then be put in a pouch or other additional packaging.

It should be understood that this disclosure is, in many respects, only illustrative. Numerous advantages of the invention covered by this document have been set forth in the foregoing description. Changes may be made in details, particularly in matters of shape, size and arrangement of parts without exceeding the scope of the invention. Those of skill in the art will readily appreciate that other embodiments may be made and used which fall within the scope of the claims attached hereto. The invention's scope is, of course, defined in the language in which the appended claims are expressed.

What is claimed is:

1. A device comprising an elongated tubular member having a first open end, a second open end and a lumen therebetween, the first end and the second end facing in the same direction and positioned so that a first end of a guidewire can extend beyond the device out of the first open end and a second end of the guidewire can extend beyond the device out of the second open end and parallel to the first end of the guidewire;

wherein a first portion of the elongated tubular member is coiled in a clock-wise direction and wherein a second portion of the elongated tubular member is coiled in a counter-clockwise direction.

2. The device of claim 1, wherein the elongated tubular member comprises a flat coil.

3. The device of claim 1, further comprising a clip holding the elongated tubular member in position.

4. The device of claim 1, wherein the elongated tubular member comprises a polymer.

* * * * *